United States Patent [19]

Balfour et al.

[11] Patent Number: 5,569,035
[45] Date of Patent: Oct. 29, 1996

[54] ENHANCED CUTTING DRILL TIP FOR ENDOSSEOUS IMPLANTS

[75] Inventors: Alan R. Balfour, Camarillo, Calif.; Francois Aeby, Ballaigues, Switzerland

[73] Assignee: Dentsply Research and Development Corp., Milford, Del.

[21] Appl. No.: 269,598

[22] Filed: Jul. 1, 1994

[51] Int. Cl.$^6$ .................................................. A61C 3/02
[52] U.S. Cl. ............................................................. 433/165
[58] Field of Search ................................. 433/165, 166, 433/173; 408/229, 230

[56] References Cited

U.S. PATENT DOCUMENTS

| | | | |
|---|---|---|---|
| 4,345,899 | 8/1982 | Vlock | 433/165 |
| 4,556,347 | 12/1985 | Barish | 408/230 |
| 4,605,347 | 8/1986 | Jodock et al. | 408/230 X |
| 4,830,000 | 5/1989 | Shutt | 408/230 X |
| 4,936,721 | 6/1990 | Meyer | 408/230 X |
| 4,943,236 | 7/1990 | Linkow et al. | 433/165 |
| 5,173,014 | 12/1992 | Agapiou et al. | 408/230 X |
| 5,261,818 | 11/1993 | Shaw | 433/165 |

OTHER PUBLICATIONS

Journal of Biomechanical Engineering, Aug. 1982, vol. 104, pp. 245–252; Surgical Drilling: Design and Performance of an Improved Drill.

*Primary Examiner*—Nicholas D. Lucchesi

[57] ABSTRACT

A tri-spade dental drill with an enhanced cutting tip for preparing surgical sites for endosseous implants is described. The cutting tip incorporates a split point cutting surface for each of the three blades wherein the split point includes a positive rake angle. All three split points converge at the center of the drill, eliminating any chisel edges. The positive rake angle split point and its offset secondary cutting flutes breaks the removed bone into smaller chips, decreasing the principle cutting force necessary for drilling and facilitating material ejection.

7 Claims, 2 Drawing Sheets

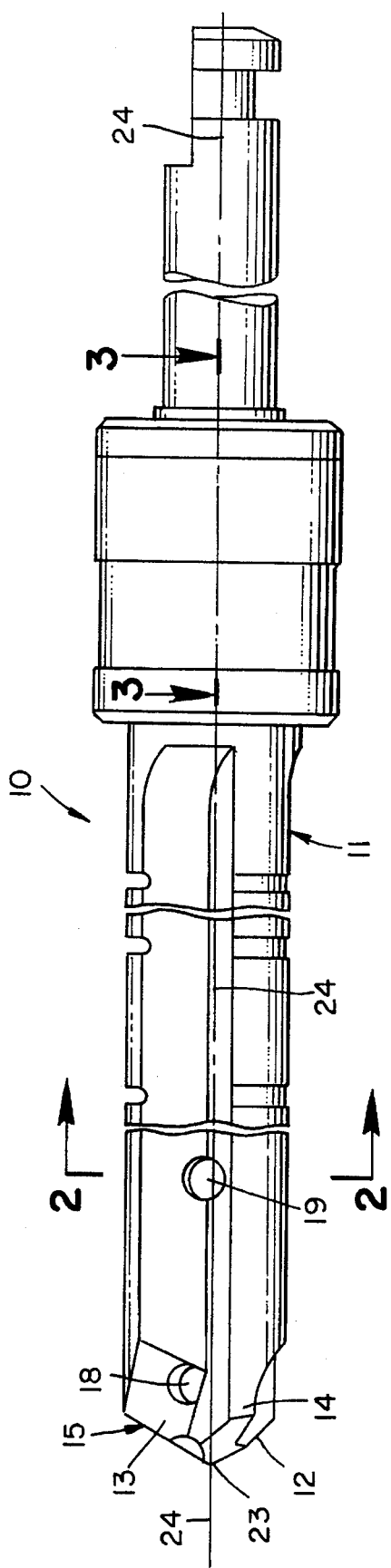
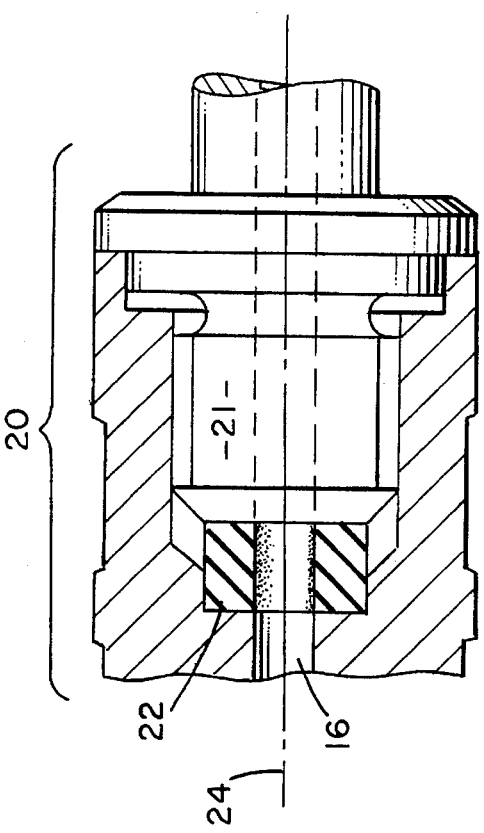
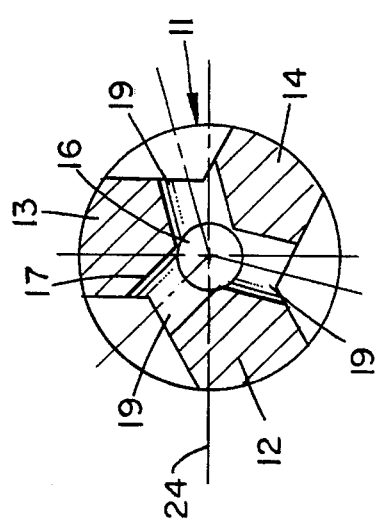

ENHANCED CUTTING DRILL TIP FOR ENDOSSEOUS IMPLANTS

BACKGROUND OF THE INVENTION

The invention relates to instruments used for preparing surgical sites in endosseous structures. More particularly, the invention relates to dental drills for endosseous implant procedures.

Dental implantation procedures require preparation of a surgical site, including penetration into bone structures. There are a number of dental implant drilling systems known, most of which are characterized by standard twist or spade drill designs.

Commercially available dental implant spade drills include a web sized chisel edge having no cutting flutes adjacent the center axis of the drill. Without cutting flutes, the tip of the drill displaces material rather than cutting it which requires a relatively high force to be applied to advance the drill.

The difficulty with prior art designs is that the force necessary to advance these conventional drill designs creates excessive frictional heating at the drill point-bone interface. This frictional heat creates a risk of the bone overheating and dying, which reduces the chance of the implants to surgically succeed.

It is desirable to optimize drill cutting surfaces to reduce the chance of overheating of the bone structure by reducing the principle cutting force needed and the time necessary to advance the drill.

SUMMARY OF THE INVENTION

A drill is described that is particularly useful for enhanced cutting in bone and preparing surgical sites for endosseous implants. The drill comprises a cylindrical shank having a plurality of blades milled therein, extending longitudinally along shank lateral surfaces, terminating in an enhanced cutting tip. A preferred drill for use in dental procedures is tri-bladed, including a tri-split point wherein the drill has no non-cutting chisel edges such that the drill cuts to the full diameter of the drill.

A positive rake angle in combination with each split point at the tip of each blade of the drill further helps decrease the principle cutting force needed for drilling. The blades primary cutting flutes are modified by the split points that form secondary cutting flutes. The combination of cutting flutes wherein the secondary flutes are offset from the primary allows chips from the drilling to break into smaller pieces facilitating their ejection from the bore up the flutes. An optimal point angle in conjunction with the positive rake angle split point decreases the torque needed for drilling.

BRIEF DESCRIPTION OF THE DRAWINGS

FIG. 1 is an elevational view of the drill of the invention.

FIG. 2 is a cross-sectional view of the drill of FIG. 1, at 2—2, showing drill blade details and internal irrigation conduits.

FIG. 3 is a cross-sectional view of the drill of FIG. 1, at 3—3, showing details of the internal irrigating conduits.

DETAILED DESCRIPTION OF PREFERRED EMBODIMENTS

Figure 4:
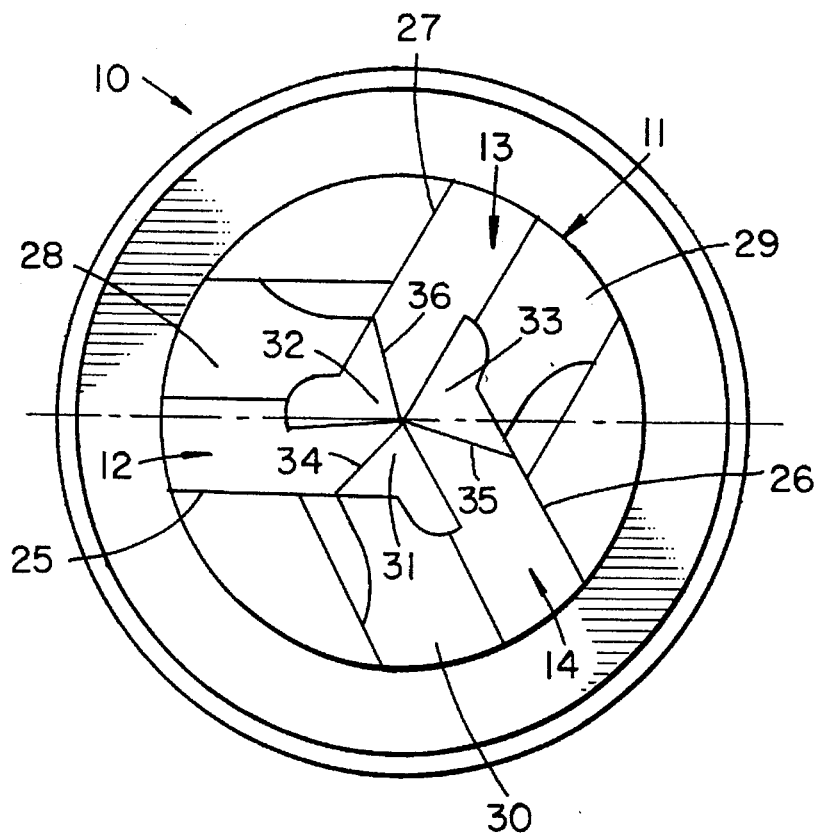
FIG. 4 is a distal end view of the drill blade cutting tip.

Referring to FIG. 1, an embodiment of the irrigated tri-spade drill 10 of the invention is shown. The drill of the invention includes a drill shank 11 in which are milled three blades 12, 13 and 14, cut into the longitudinal lateral surfaces of the shank. FIG. 2 shows the blades 12, 13, 14 in cross-section at an intermediate point 2—2 of the drill shank.

The drill of the invention includes internal passageways for irrigating portions of the drill during operation, including at the cutting tip 15 or at intermediate points such as in 2—2 along the drill shaft, as desired. Referring to FIG. 2, a central axial fluid passageway 16 is shown in combination with radial borings 17 that deliver fluid through an orifice to desired drill surfaces. As shown in FIG. 1, a fluid discharge orifice 18 at the cutting tip 15 is provided as well as an orifice 19 at an intermediate point 2—2 on the drill. FIG. 3, a sectional view of the shank at 3—3, shows an internal connection point 20 for an irrigating fluid supply conduit (not shown), including a receptacle 21 for receiving a fluid supply plug (not shown) which has a conduit that fits internally to the drill fluid passageway 16. The supply plug is frictionally secured and sealed by an internal silicone O-ring 22.

Figure 5:
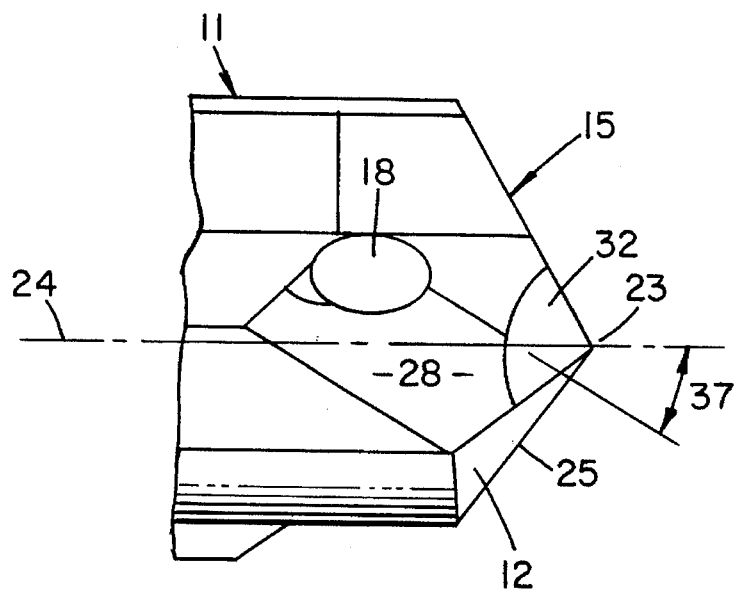
FIG. 5 is a partial elevational view of the drill tip showing the split point surface and its positive rake angle of the invention.

Referring to FIGS. 1 and 4–5, the details of the cutting tip 15 of the drill, which is a key element of the invention, are shown. A point 23 is formed at the distal, operating end of the drill having an axis coincident with the axis 24 of the shank. Point 23 is typically a standard drill point, of preferably about 120°, included angle. Milling the point 23 onto the drill forms in the blades 12, 13, 14, primary cutting flutes 25, 26, 27, converging toward the center axis of the drill. The trailing edge of each blade is milled to provide a relief 28, 29, 30, that aids chip removal during operation.

A key element of the invention is forming in each blade, by means of milling, a split point or surface 31, 32, 33, converging to the center axis of the drill to eliminate chisel edges caused by the web thickness of the drill blades. The split point surfaces form secondary cutting flutes 34, 35, 36, that are offset with respect to the primary cutting flutes 25, 26, 27. The offset, as bone is being penetrated by the drill, causes bone chips to be broken into smaller chips which facilitates chip ejection.

The secondary cutting flutes are enhanced by incorporation of a positive rake angle 37 into each split point. The rake angle is typically on the order of 10°–15° with reference to the plane of relief cut into each blade. The degree of rake depends upon the material being drilled as well as the characteristics of the drill bit material.

By eliminating the chisel edge and incorporating a positive rake into the split points, the drill cuts through its entire diameter. The result is a decreased amount of principle force required for drilling.

We claim:

1. A dental drill for use in drilling an opening in human jawbone tissue includes a cylindrical shank with lateral surfaces, said drill including a proximal end and a distal end, said drill further comprising:

a cylindrical shank, having an internal passageway for delivering a fluid to portions of said drill;

a plurality of cutting blades extending longitudinally along said shank lateral surfaces and terminating at the distal end of the drill in a cutting point converging upon the center axis of said drill; and a cutting tip at the distal end of said drill, wherein each blade comprises, a primary cutting flute comprising a relief on the trailing edge of said blade, and a secondary cutting flute formed by a split point having a positive rake angle at said blade, converging on the center axis of the drill, wherein said secondary cutting flute is offset with respect to said primary cutting flute, said split point converging to the center axis of said drill, thus precluding chisel edges on said cutting blades.

2. A dental drill for use in drilling an opening in human jawbone tissue, comprising:

a plurality of blades formed laterally on the surface of a cylindrical shank, each blade comprising a primary cutting flute and a split point converging to the center axis of the drill, said split point forming a secondary cutting flute, offset with respect to said primary cutting flute, said split point converging to the center axis of said drill, thus precluding chisel edges on said cutting blades.

3. The drill of claim 2 wherein said split point comprises a positive rake angle with respect to a trailing edge of said blade.

4. The drill of claim 3 wherein said positive rake angle is about 10°–15°.

5. The drill of claim 1 comprising three blades and three split points.

6. A method of making a tri-spade dental drill for use in drilling an opening in human jawbone tissue, comprising: milling longitudinal grooves in a cylindrical shank to form blades thereon, said grooves shaped to form a desired blade cross-section; milling a point on the distal end of the drill shank, said point forming a selective included angle with reference to the center axis of the shank; relieving each blade to a reduced width on the reverse side opposite a primary cutting flute of said blade; and milling a split point at each blade having a positive rake angle, all of said split points converging to the center axis of the drill, thus precluding a chisel edge on any of said blades, said split points forming on each blade a secondary cutting flute that is offset from the primary cutting flutes.

7. A method of using a drill for endosseous dental implants, comprising:

a plurality of blades milled into the lateral walls of a cylindrical shank, each blade comprising a primary cutting flute and a split point converging to the center axis of the drill, thus precluding a chisel edge on any of said blades, said split point forming a secondary cutting flute, offset with respect to said primary cutting flute; and utilizing said dental drill to form an opening in the jawbone of a patient of a size and shape suitable for receiving a dental implant.

* * * * *